(12) United States Patent
Cheng

(10) Patent No.: US 10,053,676 B2
(45) Date of Patent: Aug. 21, 2018

(54) ARGININE IMPROVES POLYMERASE STORAGE STABILITY

(71) Applicant: Bio-Rad Laboratories, Inc., Hercules, CA (US)

(72) Inventor: Man Cheng, Danville, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 307 days.

(21) Appl. No.: 14/817,064

(22) Filed: Aug. 3, 2015

(65) Prior Publication Data

US 2016/0145587 A1 May 26, 2016

Related U.S. Application Data

(60) Provisional application No. 62/084,505, filed on Nov. 25, 2014.

(51) Int. Cl.
*C12Q 1/68* (2018.01)
*C12N 9/12* (2006.01)
*C12N 9/96* (2006.01)

(52) U.S. Cl.
CPC ............ *C12N 9/1252* (2013.01); *C12N 9/96* (2013.01); *C12Y 207/07* (2013.01); *C12Y 207/07007* (2013.01)

(58) Field of Classification Search
CPC .................................................. C12N 9/1252
USPC ....................................................... 435/6.12
See application file for complete search history.

(56) References Cited

U.S. PATENT DOCUMENTS

| | | | |
|---|---|---|---|
| 6,127,155 A | 10/2000 | Gelfand et al. | |
| 7,422,882 B2 | 9/2008 | Kuroita et al. | |
| 8,835,146 B2 | 9/2014 | Battrell et al. | |
| 2008/0064071 A1 | 3/2008 | Hogrefe et al. | |
| 2010/0099150 A1 | 4/2010 | Fang et al. | |
| 2012/0142070 A1 | 6/2012 | Battrell et al. | |
| 2013/0224793 A1 | 8/2013 | Martin et al. | |

FOREIGN PATENT DOCUMENTS

| | | |
|---|---|---|
| WO | 2009/006301 A2 | 1/2009 |
| WO | 2014/100755 A2 | 6/2014 |
| WO | 2014/144682 A1 | 9/2014 |

OTHER PUBLICATIONS

Hjelmeland, "A nondenaturing zwitterionic detergent for membrane biochemistry: Design and synthesis", Nov. 1980, vol. 77, No. 11 pp. 6368-6370, Proc. Natl. Acad. Sci. USA.
International Search Report and Written Opinion dated Jan. 28, 2016 for International Patent Application No. PCT/US2015/043421, 12 pages.
Extended European Search Report from EP Appln. 15863137.4 dated Mar. 2, 2018; 9 pages.
Baynes, B.M. et al.; "Role of Arginine in the Stabilization of Proteins against Aggregation"; *Biochemistry*; vol. 44, No. 12; Mar. 1, 2005; pp. 4919-4925; American Chemical Society.
Hamada, H. et al.; "L-Argininamide improves the refolding more effectively than L-arginine"; *Journal of Biotechnology*; vol. 130, No. 2; Jun. 15, 2007; pp. 153-160; Elsevier, Amsterdam, NL.
Ohtake, S. et al.; "Interactions of formulation excipients with proteins in solution and in the dried state"; *Advanced Drug Delivery Reviews*; vol. 63, No. 13; Jun. 23, 2011; pp. 1053-1073; Elsevier, Amsterdam, NL.

*Primary Examiner* — Jezia Riley

(74) *Attorney, Agent, or Firm* — Kilpatrick Townsend and Stockton LLP

(57) ABSTRACT

Liquid storage solutions comprising polymerases are provided.

23 Claims, 6 Drawing Sheets

SEQUENCE LISTING

```
<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(12)
<223> OTHER INFORMATION: N is A, T, C or G

<400> SEQUENCE: 1
cgannnnnnt gc                                                            12
```

ARGININE IMPROVES POLYMERASE STORAGE STABILITY

CROSS-REFERENCE TO RELATED PATENT APPLICATIONS

The present patent application claims benefit of priority to U.S. Provisional Patent Application No. 62/084,505, filed Nov. 25, 2014, which is incorporated by reference.

BACKGROUND OF THE INVENTION

Native or recombinant thermostable polymerase has been widely used in thermal cycling chain reaction, e.g. PCR or qPCR, for various applications. For long-term storage stability, thermostable polymerases are generally stored in buffer containing one or more non-ionic detergents, e.g. NP-40, Tween 20, and Triton X. See, e.g., U.S. Pat. No. 6,127,155. Zwitterionic detergents, e.g. CHAPS, CHAPSO and Surfynol, have also been found to enhance polymerase storage stability and activity according to US patent application 2008/0064071 A1 and 2010/0099150 A1, despite previous publications suggesting zwitterionic detergents, such as CHAPS, can potentially cause protein denaturation (Hjelmeland, 1980).

BRIEF SUMMARY OF THE INVENTION

In some embodiments, provided herein are liquid storage solution for storing a polynucleotide manipulating enzyme (e.g., a polymerase or other enzyme as described herein). In some embodiments, the solution comprises, the enzyme (e.g., polymerase or restriction enzyme); free arginine or a salt thereof or an arginine derivative (for example, but not limited to arginine ethyl ester, argininamide dihydrochloride) or a salt thereof; and 5% or more cryoprotectant. In some embodiments, the cryoprotectant is a diol, triol, polyalcohol, monodydric alcohol or a sulfoxide. In some embodiments, the free arginine or a salt thereof or an arginine derivative or a salt thereof is at a concentration of 0.01-5 M (e.g., 0.01-2.5 M).

In some embodiments, the storage solution further comprises one or more of a buffer, KCl, ethylenediaminetetraacetic acid (EDTA), or dithiothreitol (DTT). In some embodiments, the liquid solution comprises the buffer and the buffer is a Goods buffer. In some embodiments, the Goods buffer is selected from the group consisting of MES, BIS-TRIS, ADA, ACES, PIPES, Bis-6Tris Propane, MOPSO, BES, MOPS, TES, HEPES, DIPSO, MPOS, TAPSO, HEPPSO, POPSO, EPPS, Tricine, TRIS, AMP, Bicarbonate, Bicine, Borate, Cacodylate, CAPS, CAPSO, CHES, Citrate, DIPSO, Glycine, Glycylglycine, Phosphate, TAPS, TAPSO, and TEA.

In some embodiments, the arginine or salt thereof or arginine derivative or salt thereof is at a concentration of 0.1-1.0 M.

In some embodiments, the solution lacks sufficient ingredients to sustain polymerization of a template polynucleotide. In some embodiments, the solution lacks at least one of: the template polynucleotide; or oligonucleotide primers.

In some embodiments, the solution is at a temperature of −80 to 5° C. In some embodiments, the solution is at a temperature of −30 to 5° C. In some embodiments, the solution is at a temperature of −80 to 10° C. In some embodiments, the solution is at a temperature of −80 to 50° C. In some embodiments, the solution is at a temperature of −80 to 90° C. In some embodiments, the solution is at a temperature of −80 to 100° C.

In some embodiments, the solution is free of detergents. In some embodiments, the solution comprises one or more detergent.

In some embodiments, the solution is free of trisaccharides.

In some embodiments, the polymerase is a thermostable polymerase.

In some embodiments, the polymerase is a reverse transcriptase.

In some embodiments, the polymerase is or comprises a Family B polymerase.

Also provided is a method of maintaining stability of a polymerase during storage. In some embodiments, the method comprises providing the liquid solution as described above or elsewhere herein; and storing the solution for at least three (e.g., at least 7, 14, 21, 28, 50, 100) days. In some embodiments, the storing occurs at between −80 and 5° C. In some embodiments, the storing occurs at between −80 and 10° C. In some embodiments, the storing occurs at between −80 and 50° C. In some embodiments, the storing occurs at between −80 and 90° C. In some embodiments, the storing occurs at between −80 and 100° C. In some embodiments, the method further comprises following the storing, using the polymerase in an enzymatic reaction.

For example, in some embodiments, the method comprises providing a liquid solution comprising the enzyme (e.g., polymerase or restriction enzyme) and 0.01-5.0 M arginine or a salt thereof or arginine derivative or salt thereof; and storing the solution for at least three (e.g., at least 7, 14, 21, 28, 50, 100) days. In some embodiments, the storing occurs at between −80 and 5° C. In some embodiments, the storing occurs at between −80 and 10° C. In some embodiments, the storing occurs at between −80 and 50° C. In some embodiments, the storing occurs at between −80 and 90° C. In some embodiments, the storing occurs at between −80 and 100° C. In some embodiments, the method further comprises, following the storing, using the polymerase in an enzymatic reaction.

Definitions

The term "polymerase" refers to an enzyme that performs synthesis of polynucleotides. In some embodiments, the polymerase is a template-dependent polymerase. In some embodiments, the polymerase is a template-independent polymerase (e.g., a terminal transferase or poly A polymerase). The term encompasses both a full length polypeptide and a domain that has polymerase activity. DNA polymerases are well-known to those skilled in the art, including but not limited to DNA polymerases isolated or derived from *Pyrococcus furiosus*, *Thermococcus litoralis*, and *Thermotoga* maritime, or modified versions thereof. They include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

"Thermally stable polymerase" or "thermostable polymerase," as used herein, refers to any enzyme that catalyzes polynucleotide synthesis by addition of nucleotide units to a nucleotide chain using DNA or RNA as a template and has an optimal activity at a temperature between 45° C. and 100° C.

The term "nucleic acid amplification" or "amplification reaction" refers to any in vitro means for multiplying the copies of a target sequence of nucleic acid. Such methods include but are not limited to polymerase chain reaction (PCR), DNA ligase chain reaction (see U.S. Pat. Nos. 4,683,195 and 4,683,202; PCR Protocols: A Guide to Methods and Applications (Innis et al., eds, 1990)), (LCR), QBeta RNA replicase, and RNA transcription-based (such as TAS and 3SR) amplification reactions as well as others known to those of skill in the art.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term amplifying typically refers to an "exponential" increase in target nucleic acid. However, amplifying as used herein can also refer to linear increases in the numbers of a select target sequence of nucleic acid, such as is obtained with cycle sequencing.

An "olignucleotide primer" or "primer" refers to an oligonucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides in length. The length and sequences of primers for use in PCR can be designed based on principles known to those of skill in the art; see, e.g., Innis et al., supra.

A "template" refers to a polynucleotide sequence that comprises the polynucleotide to be amplified, flanked by primer hybridization sites. Thus, a "target template" comprises the target polynucleotide sequence flanked by hybridization sites for a 5' primer and a 3' primer.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide nucleic acids (PNAs).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

DETAILED DESCRIPTION OF THE INVENTION

Introduction

Figure 1:
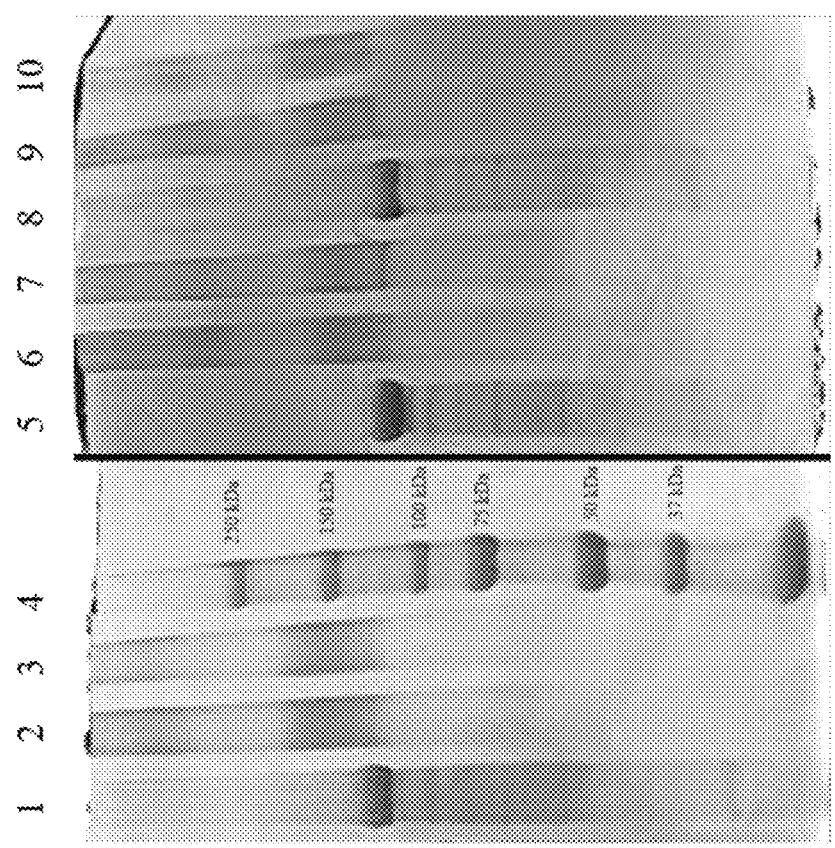
FIG. 1 shows SDS-PAGE analysis of DNA polymerase stability in storage buffer supplemented with various detergent. Lane 1 and 2 are Pi DNA polymerase in CHAPS zwitterionic detergent storage buffer stored at −20 C and 55 C for 24 hours, respectively; Lane 3 is Pi DNA polymerase in CHAPS zwitterionic detergent storage buffer supplemented with 2× protease inhibitor cocktail and stored at 55 C for 24 hours; Lane 4 is protein ladder; Lane 5 and 6 are Tau DNA polymerase in CHAPS zwitterionic detergent storage buffer stored at −20 C and 55 C for 24 hours, respectively; Lane 7 is Tau DNA polymerase in CHAPS zwitterionic detergent storage buffer supplemented with 2× protease inhibitor cocktail and stored at 55 C for 24 hours; Lane 8 and 9 are Tau DNA polymerase in NP40 and Tween20 non-ionic polymeric detergent storage buffer stored at −20 C and 55 C for 24 hours, respectively; Lane 10 is Tau DNA polymerase in NP40 and Tween20 non-ionic polymeric detergent storage buffer supplemented with 2× protease inhibitor cocktail and stored at 55 C for 24 hours.

The inventor has surprisingly discovered that arginine and arginine derivatives can be used in liquid storage solutions to stabilize enzymes that manipulate polynucleotides. For example, the inventor has discovered that arginine or arginine derivatives can stabilize polymerases during storage. The enzyme stability observed in the presence of arginine and arginine derivatives occurs in the absence or presence of detergents. The effect of arginine on polymerase stability is surprisingly strong, resulting in a solution that can be stored at least nine times longer compared a control lacking arginine.

Arginine and Arginine Derivatives

Free arginine (e.g., L-arginine or D-arginine, not linked to another amino acid) or arginine derivatives can be used in a polymerase storage solution to stabilize the polymerase in the solution. The concentration of arginine or arginine derivative used in the storage solution can vary and is provided in a concentration to increase stability. In some embodiments, the concentration is 0.01-5 M, 0.1-2.0 M, e.g., 0.1-1.0 M, 0.5-1.5 M, 0.6-0.9 M, etc.

A number of arginine derivatives are known. In some embodiments, the arginine derivative comprises arginine but includes one or more additional moiety (e.g., a methyl or hydroxyl in the arginine carbon backbone (e.g., 5-methyl-arginine or c-gamma-hydroxy arginine). Other exemplary arginine derivatives include, for example, citrulline. 2-Amino-3-guanidinobutyric acid, 2-Amino-4-guanidinobutyric acid, cavanine, homoarginine, thio-citrulline, L-2-Amino-3-guanidinopropionic acid, 4-guanidinobutyric acid, 3-guanidinobutyric acid. The inventor has shown, for example, that inclusion of arginine ethyl ester or argininamide dihydrochloride improve enzyme stability.

The arginine or arginine derivatives may be provided as salts. Examples of applicable salt forms include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures), succinates, and benzoates. These salts may be prepared by methods known to those skilled in art. Also included are base addition salts such as sodium, potassium, calcium, ammonium, organic amino, or magnesium salt, or a similar salt. When an agent of the present invention contains relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. In some embodiments, arginine salts are monohydrochloride, dihydrochloride, trihydrochloride, or tetrahydrochloride salts.

Storage stability of a polymerase, and thus improvement of storage stability relative to a control, can be measured for example by incubating the polymerase in the storage solution for 24 hours at 55° C. and then measuring the ability of the polymerase to amplify a template using qPCR. An increase in Ct or Cq values of a polymerase in storage indicates the activity of the polymerase has degraded, with the absolute value of the change in Ct or Cq indicating the amount of degradation. Stability tests can also be performed at ambient temperature, 0° C. or lower for longer periods of time. Inclusion of arginine or arginine derivative in the storage solution will result in a smaller increase in Cq or Ct compared to a control storage solution lacking arginine or arginine derivative.

Polynucleotide Manipulating Enzymes

The present disclosure provides for stabilization of a variety of polynucleotide-manipulating enzymes. Examples of polynucleotide-manipulating enzymes include, but are not limited to, template-dependent polymerases, polymerase-independent polymerases, and DNA cleaving enzymes (e.g., restriction enzymes or DNases).

Template-Dependent Polymerases

A variety of template-dependent polymerases can be used. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases. Any of these polymerases, combinations of, or portions of, these polymerases, as well as chimeras or hybrids between two or more of such polymerases or their equivalents can be used in the storage solutions described herein.

In some embodiments, the polymerase has a non-naturally-occurring polypeptide sequence. For example, in some embodiments, the polymerase comprises one or more non-naturally-occurring mutations that improve a desired polymerase activity (e.g., specificity, efficiency, etc.) or is a fusion or chimera. In some embodiments, the polymerase is recombinantly produced.

In some embodiments, the polymerase is thermostable. Further, in some embodiments, non-thermostable polymerases may also be used in accordance with the invention. For example, the large fragment of *E. coli* DNA Polymerase I (Klenow) (the Klenow Fragment) with mutation (D355A, E357A) abolishes the 3'-5' exonuclease activity.

In one exemplary embodiment, the polymerase has a polymerase domain derived from two parental polymerases, Pfu and DeepVent. Such polymerases are described for example in U.S. Application Publication Nos. 20040219558; 20040214194; 20040191825; 20030162173, each of which is hereby incorporated by reference in its entirety for all purposes and in particular for all teachings related to hybrid polymerases.

In some embodiments, a polymerase is part of a polymerase conjugate including a polymerase domain comprising mutations that reduce or abolish exonuclease activity of a polymerase comprising such a polymerase domain in comparison to a polymerase comprising a polymerase domain that does not have such mutations. A variety of mutations can be introduced into a native polymerase domain to reduce or eliminate 3'-5' exonuclease activity. For example, U.S. Pat. Nos. 6,015,668; 5,939,301 and 5,948,614 describe mutations of a metal-binding aspartate to an alanine residue in the 3'-5' exonuclease domain of the Tma and Tne DNA polymerases. These mutations reduce the 3'-5' exonuclease activities of these enzymes to below detectable levels. Similarly, U.S. Pat. No. 5,882,904 describes an analogous aspartate-to-alanine mutation in *Thermococcus barossi*, and U.S. Pat. No. 5,489,523 teaches the double-mutant D141A E143A of the *Pyrococcus wosei* DNA polymerases. Both of these mutant polymerases have virtually no detectable 3'-5' exonuclease activity. Methods of assaying 3'-5' exonuclease activity are well-known in the art. See, e.g., Freemont et al., Proteins 1:66 (1986); Derbyshire et al., EMBO J. 16:17 (1991) and Derbyshire et al., *Methods in Enzymology* 262: 363 85 (1995). It will be understood that while the above-described mutations were originally identified in one polymerase, one can generally introduce such mutations into other polymerases to reduce or eliminate exonuclease activity. "Exonuclease deficient," as used herein, means that the polymerase has a substantially reduced exonuclease activity (i.e., less than 10%, 5%, or 1% of 3'-5' exonuclease activity as compared to a wild-type polymerase) or no exonuclease activity).

In some embodiments, the nucleic acid amplification methods of the present invention utilize a polymerase polypeptide or domain conjugated to a DNA binding domain or protein, e.g., a Sso7 or Sso7-like domain. Such polymerase conjugates are known to show an increased processivity. See, e.g., U.S. patent application Ser. No. 12/683,950, the contents of which are hereby incorporated by reference in its entirety for all purposes and in particular for all teachings related to polymerases, polymerase conjugates, as well as all methods for making and using such polymerases.

Sso7d and Sac7d are small (about 7 kDa MW), basic chromosomal proteins from the hyperthermophilic archaeabacteria *Sulfolobus solfataricus* and *S. acidocaldarius*, respectively (see, e.g., Choli et al., *Biochimica et Biophysica Acta* 950:193-203, 1988; Baumann et al., *Structural Biol.* 1:808-819, 1994; and Gao et al, *Nature Struc. Biol.* 5:782-786, 1998). These proteins bind DNA in a sequence-independent manner and when bound, increase the $T_m$ of DNA by up to 40° C. under some conditions (McAfee et al., Biochemistry 34:10063-10077, 1995). Sso7 proteins and their homologs are typically believed to be involved in stabilizing genomic DNA at elevated temperatures. Sso7d, Sac7d, Sac7e and related sequences (referred to herein as "Sso7 proteins" or "Sso7 domains") are known in the art (see, e.g., UniProt database accession numbers: P39476 (Sso7d); O59632 (Ssh7b); P13123 (Sac7d); P13125 (Sac7e); and Q96X56 (Stole)). In some embodiments, Sso7 or Sso7-like domains or proteins are modified from the wild-type Sso7 by making one or more mutations in the Sso7 DNA binding domain. See, e.g., WO 2012/138417.

In some embodiments, the polymerase comprises a polymerase that does not naturally have a 5'-3' exonuclease activity fused with a heterologous 5'-3' exonuclease domain to generate a fusion protein that retains both polymerase and 5'-3' exonuclease activity. In some embodiments, a 5'-3' exonuclease domain is fused to the amino terminus of a family B polymerase, optionally via a linker.

A variety of domains having 5'-3' exonuclease activity are known and can be used in the fusion proteins as described herein. In some embodiments, the 5'-3' exonuclease domain is a flap endonuclease (FEN1) or a fragment thereof retaining 5'-3' exonuclease activity. FEN1 proteins are generally from Eukarya and Archea and possess 5'-3' exonuclease activity. A variety of FEN1 proteins (as well as active fragments or variants thereof) are known (see, e.g., Williams, et al., *J. Mol. Biol.* 371(1):34-38 (2007)) and can be used as the 5'-3' exonuclease domain as described herein. In some embodiments the FEN1 protein has thermostable 5'-3' exonuclease activity. Theremostable FEN1 proteins include, but are not limited to, the *Methanococcus jannaschii* FEN1 protein (see, e.g., Rao, et al., *J. Bacteriol.* 180(20):5406-5412 (1998)), the *Pyrococcus furiosus* FEN1 protein (see, e.g., Hosfield, et al., *Cell* 95:135-146 (1998)) or the *Desulfurococcus amylolyticus* FEN1 protein (see, e.g., Mase et al., *Acta Crystallographica Section F* F67:209-213 (2011), as well as active variants (e.g., substantially identical versions thereof) or fragments thereof. An exemplary active FEN1 protein fragment is a FEN1 protein that lacks a PCNA-interacting protein motif (PIP) box. PIP boxes are described in, e.g., Querol-Audi, et al., *Proc. Natl. Acad. Sci USA* 109(22):8528-8533 (2012).

In some embodiments, the 5'-3' exonuclease domain is from a heterologous polymerase. For example family A polymerases have 5'-3' activity and thus fragments of a family A polymerase can be used as the 5'-3' exonuclease domain. Conserved sites within the 5'-3' exonuclease domain of the *E. coli* polymerase (Pol I) has been described. See, e.g., Gutman et al., *Nucleic Acids Res.* 21(18):4406-7 (1993). The 5'-3' exonuclease domain of various thermostable polymerases have also been identified and separately expressed with retained activity. See, e.g., Choi et al., *Biotechnol. Letts.* 23:1647-52 (2001) and Kaiser et al., *J. Chem. Biol.* 274(30):21387-21394 (1999). An exemplary listing of sources of 5'-3' exonuclease domains useful in the protein fusions described herein include, but are not limited to, *Thermus thermophilus* (Tth) DNA polymerase, *Thermus aquaticus* (Taq) DNA polymerase, *Thermotoga neopolitana* (Tne) DNA polymerase, *Bacillus stearothermophilus* DNA polymerase, and *Thermotoga maritima* (Tma) DNA polymerase, and mutants, and variants (e.g., substantially identical versions thereof) and derivatives thereof.

Exemplary polymerases useful in the fusions described above include, but are not limited to, *Pyrococcus horikoshii* (e.g., accession number O59610), *P. abyssi* (e.g., accession number P77916), *P. glycovorans* (e.g., accession number CAC12849), *Pyrococcus* sp. GE23 (e.g., accession number CAA90887), *Pyrococcus* sp. GB-D (e.g., accession number Q51334), *P. furiosus* (e.g., accession number P61875), *P. woesei* (e.g., accession number P61876), *Thermococcus kodakaraensis* (e.g., accession number P77933), *T. gorgonarius* (e.g., accession number P56689), *T. fumicolans* (e.g., accession number P74918), T. sp. 9oN-7 (e.g., accession number Q56366), *T. onnurineus* NA1 (e.g., accession number ABC11972), *T. litoralis* (e.g., accession number P30317), and *T. aggregans* (e.g., accession number O33845), as well as fragments and variants (e.g., substantially identical versions thereof) thereof that retain polymerase activity. In some embodiments, the polymerase is derived from two parental polymerases, e.g., Pfu and DeepVent. Such polymerases are described for example in U.S. Application Publication Nos. 20040219558; 20040214194; 20040191825; 20030162173

In some embodiments, the template-dependent polymerase is an RNA polymerase. In some embodiments, the RNA polymerase is a reverse polymerase. Exemplary reverse transcriptases include but are not limited to murine leukemia virus (MLV) reverse transcriptase, Avian Myeloblastosis Virus (AMV) reverse transcriptase, Respiratory Syncytial Virus (RSV) reverse transcriptase, Equine Infectious Anemia Virus (EIAV) reverse transcriptase, Rous-associated Virus-2 (RAV2) reverse transcriptase, SUPERSCRIPT II reverse transcriptase, SUPERSCRIPT I reverse transcriptase, THERMOSCRIPT reverse transcriptase and MMLV RNase if reverse transcriptases.

Template-Independent Polymerases

In some embodiments, the polynucleotide manipulating enzyme is a template-independent polymerase. Exemplary template-independent polymerases include, for example, terminal transferases or poly A polymerases. An exemplary terminal transferase includes but is not limited to terminal transferase TdT. An exemplary poly A polymerase includes but is not limited to *E. coli* poly A polymerase.

Restriction Enzymes

In some embodiments, the polynucleotide manipulating enzyme is a restriction enzyme. Thus, in these embodiments, the modification introduced into the genomic DNA is a sequence-specific single-stranded (e.g., a nick) or double-stranded cleavage event. A wide variety of restriction enzymes are known and can be used in the present invention.

Any type of restriction enzyme can be used. Type I enzymes cut DNA at random far from their recognition sequences. Type II enzymes cut DNA at defined positions close to or within their recognition sequences. Some Type II enzymes cleave DNA within their recognition sequences. Type II-S enzymes cleave outside of their recognition sequence to one side. The third major kind of type II enzyme, more properly referred to as "type IV," cleave outside of their recognition sequences. For example, those that recognize continuous sequences (e.g., AcuI: CTGAAG) cleave on just one side; those that recognize discontinuous sequences (e.g., BcgI: CGANNNNNNTGC; SEQ ID NO:1) cleave on both sides releasing a small fragment containing the recognition sequence. Type III cleave outside of their recognition sequences and require two such sequences in opposite orientations within the same DNA molecule to accomplish cleavage.

Cryoprotectants

A cryoprotectant is a substance used to protect an enzyme (e.g., a polymerase) from freezing damage. Exemplary cryoprotectants include, but are not limited to polyols, including e.g., diols, triols; polyalcohols; monodydric alcohols; monosaccharides; polysaccharides; or sulphoxides. Exemplary glycol cryoprotectants include, for example, ethylene glycol, propylene glycol, and glycerol. Other cryoprotectants include, for example, dimethylsulfoxide (DMSO).

In some embodiments, the cryoprotectant is included in the storage solution at a concentration of 5-80%, e.g., 10-80%, 10-60%, 25-70%, etc.

Other Ingredients

In some embodiments, the storage solution is a liquid solution having only a cryoprotectant, arginine or an arginine derivative, and the polymerase. In some embodiments, the storage solution contains additional ingredients.

For example, in some embodiments, the storage solution further comprises one or more buffer. In some embodiments, the buffer is a "Good" buffer (Good, N. E. et al. (1966)

Biochemistry 5, 467-477; Good, N. E. & Izawa, S. (1972) Methods Enzymol. 24, 53-68; Ferguson, W. J. et al. (1980) Anal. Biochem. 104, 300-310). Exemplary Good buffers include, e.g., MES, BIS-TRIS, ADA, ACES, PIPES, Bis-6Tris Propane, MOPSO, BES, MOPS, TES, HEPES, DIPSO, MPOS, TAPSO, HEPPSO, POPSO, EPPS, Tricine, TRIS, AMP, Bicarbonate, Bicine, Borate, Cacodylate, CAPS, CAPSO, CHES, Citrate, DIPSO, Glycine, Glycylglycine, Phosphate, TAPS, TAPSO, and TEA.

Buffers can be included in an amount useful for the ultimate use of the enzyme as well as for improving storage stability. Depending on the use of the stored enzyme, buffer concentrates of the storage solution can be at a concentration for use, or at a "stock" concentration, e.g., 10×, 50×, 100×, etc of the optimal concentration of the enzyme.

In some embodiments, the storage solution will lack one or more ingredient such that the storage solution does not support polymerization of a polynucleotide without the ingredient(s) being added later. For example, in some embodiments, the storage solution lacks one or more of a template polynucleotide or oligonucleotide primers.

In some embodiments, the storage solution lacks a detergent (for example, is free of a zwitterionic detergent, is free of a nonionic detergent), etc. In some embodiments, the storage solution lacks a trisaccharide.

The storage solution can be stored at a variety of temperatures as desired, with temperatures below 4° C. being desired in some embodiments. The storage solutions can be stored at, for example a temperature of −80° to 5° C., or −30° to 5° C. for at least 1, 2, 3, 4, 5, 6, 7, 8, 9, 10 weeks and up to 1, 2, 3, 4 or 5 years.

Also provided are kits comprising the stabilized polymerase solutions described herein.

Examples

The following examples are intended to illustrate, but not to limit, the claimed invention.

Using two thermostable DNA polymerases, Pi and Tau, polymerase stability was shown be improved by supplementing a storage buffer with arginine or an arginine derivative, e.g. arginiamide and arginine ethyl ester. The protective or stabilizing effect of arginine was so prominent that its presence significantly enhanced polymerase stability and extended storage shelf-life by 9-fold, and exceeded stability achieved by either non-ionic polymeric detergent or zwtterionic detergent supplements. Pi polymerase refers to a fusion of the 5'-3' exonuclease domain of flap endonuclease (FEN1) linked to a Pfu/Vent-hybrid DNA polymerase which in turn is fused to a carboxyl terminal Sso7d domain with a K28 mutation (SEQ ID NO: 22) and then a poly-His tag. Tau polymerase refers to a fusion of the 5'-3' exonuclease domain of Taq polymerase linked to a Pfu/Vent-hybrid DNA polymerase which in turn is fused to a carboxyl terminal Sso7d domain with a K28 mutation (SEQ ID NO: 22) and then a poly-His tag.

Non-ionic and zwitterionic detergents have been described to improve storage stability of thermostable polymerase. See, e.g., U.S. Pat. No. 6,127,155 and US Patent Application No. 2008/0064071. However, SDS-PAGE analysis revealed that DNA polymerase, Pi and Tau, were not stable in a polymerase storage buffer containing either detergents. As shown in FIG. 1, upon heating at 55° C. for 24 hours, both Pi and Tau DNA polymerases were destabilized in storage buffer containing either CHAPS zwitterionic detergent or a blend of NP40/Tween20 non-ionic detergents. This destabilization of Pi and Tau storage stock upon heating was not related to protease activity as storage buffer supplemented with 2× protease inhibitor cocktail provided no protection. Based on real-time stability test, the maximum storage stability of Pi DNA polymerase in CHAPS detergent containing storage buffer is only 39 days at 4° C. degree.

Figure 2:
FIG. 2 shows stability of DNA polymerase in storage buffer supplemented with various detergent and its PCR performance. Lane 3 and 9 are Pi DNA polymerase in CHAPS zwitterionic detergent storage buffer stored at −20 C and 55 C for 24 hours respectively; Lane 4 and 10 are Pi DNA polymerase in CHAPS zwitterionic detergent storage buffer supplemented with Octyl-B-D-glucopyranoside non-ionic detergent stored at −20 C and 55 C for 24 hours respectively; Lane 5 and 11 are Tau DNA polymerase in CHAPS zwitterionic detergent storage buffer stored at −20 C and 55 C for 24 hours respectively; Lane 6 and 12 are Tau DNA polymerase in NP40 and Tween-20 non-ionic detergent storage buffer stored at −20 C and 55 C for 24 hours respectively; Lane 7 is 100 bp DNA ladder; Lane 8 is PCR control using SciProof DNA polymerase; * Same result was obtained with storage at 45 C for 24 hrs and 35 C for 48 hrs (data not shown).

Functional testing by using PCR demonstrated a correlation between polymerase storage stability and functional activity. As shown in FIG. 2, both Pi and Tau thermostable DNA polymerases lost their polymerase activity upon heating at 55° C. for 24 hours in storage stock containing either CHAPS or a blend of NP40/Tween20 detergents. Supplement of non-ionic detergent, Octyl-B-D-glucopyranoside had no effect in restoring polymerase activity.

Figure 3:
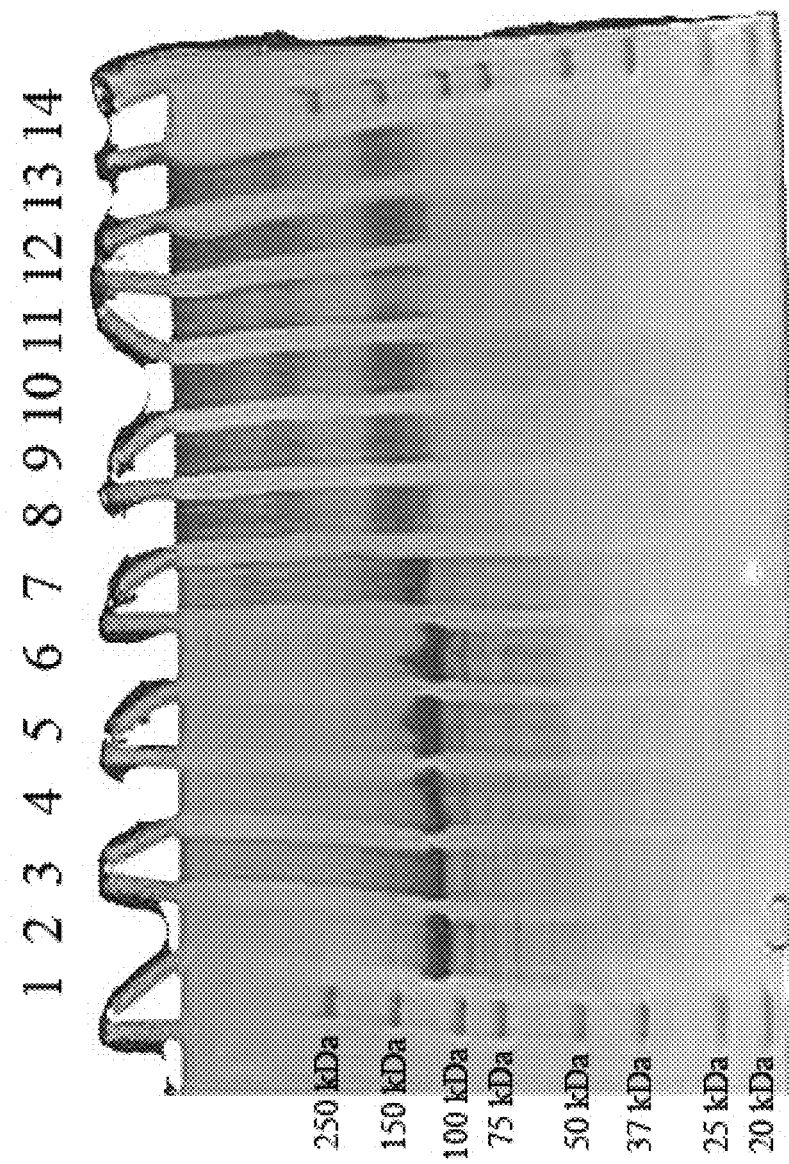
FIG. 3 shows SDS-PAGE analysis of DNA polymerase stability in storage buffer supplemented with various detergent. Each lane contains 100 unit of polymerase. Lane 1 and 14 are protein ladder; Lane 2 and 8 are Pi DNA polymerase in CHAPS zwitterionic detergent storage buffer stored at −20 C and 55 C for 24 hours, respectively; Lane 3 and 9 are Pi DNA polymerase in CHAPS zwitterionic detergent storage buffer supplemented with Octyl-B-D-glucopyranoside nonionic detergent stored at −20 C and 55 C for 24 hours, respectively; Lane 4 and 10 are Pi DNA polymerase in CHAPS zwitterionic detergent storage buffer supplemented with SDS ionic detergent stored at −20 C and 55 C for 24 hours, respectively; Lane 5 and 11 are Pi DNA polymerase in CHAPS zwitterionic detergent storage buffer supplemented with CTAB ionic detergent stored at −20 C and 55 C for 24 hours, respectively; Lane 6 and 12 are Pi DNA polymerase in CHAPS detergent storage buffer supplemented with SDS and CTAB ionic detergent stored at −20 C and 55 C for 24 hours, respectively; Lane 7 and 13 are Pi DNA polymerase in CHAPS detergent storage buffer supplemented with NP40 and Tween20 nonionic polymeric detergent stored at −20 C and 55 C for 24 hours, respectively.

To identify a superior supplement, we performed SDS-PAGE analysis of polymerases in storage buffer containing various detergents, including non-ionic (Octyl-B-D-glucopyranoside, NP40, Tween20), ionic (SDS, CTAB), and zwitterionic (CHAPS) detergents, and compared polymerase stability in storage buffer at raised temperature to the same buffer stored at −20° C. degree. As indicated in FIG. 3, none of the tested detergents showed stability enhancement effect on thermostable Pi DNA polymerase.

We later tested several additives including non detergent sulfobetaine, polyvinylpyrrolidone, polyamine, amine oxide, arginine and arginine derivatives. Among all tested additives, only arginine and its derivatives, including arginiamide ethyl ester and arginiamide, were found to be effective in enhancing storage stability of both Pi and Tau DNA polymerase (Table 1).

TABLE 1

| Group | Type | Name | Effect |
|---|---|---|---|
| 1 | Non-ionic detergent | Octyl-B-D-glucopyranoside | No effect |
| | | NP40 | No effect |
| | | Tween20 | No effect |
| 2 | Ionic detergent | SDS | No effect |
| | | CTAB | No effect |
| 3 | Non detergent Sulfobetaine | NDSB-221 | No effect |
| 4 | Salt | Magnesium Chloride | No effect |
| | | Calcium Chloride | No effect |
| | | Ammonium Chloride | No effect |
| 5 | Polymer | PVP | No effect |
| 6 | Polyamine | Spermidine | No effect |
| 7 | Amine Oxide | Tetra Methyl Amine N-Oxide | No effect |
| 8 | Arginine derivatives | Arginine Ethyl Ester Dihydrochloride | Slightly improve stability |
| | | Arginiamide Dihydrochloride | Moderately improve stability |
| | | Arginine | Significantly improve stability | qPCR based functional analysis using Pi DNA polymerase in CHAPS-storage buffer supplemented with arginine or its derivatives showed significant improvement in polymerase activity as reflected from dCq value, which compared polymerase stocks preheated at 55° C. versus stocks stored at −20° C. degree. Arginine consistently showed prominent stability enhancement effect (Table 2).

TABLE 2

| | Cq delay (dCq value of 55 C. subtract −20 C.) |
|---|---|
| Control - No additive supplemented | n.d. |
| +0.1M Arginine | 1.18 |

TABLE 2-continued

| | Cq delay (dCq value of 55 C. subtract −20 C.) |
|---|---|
| +0.1M Arginine Ethyl Ester Dihydrochloride | 9.14 |
| +0.1M Arginiamide Dihydrochloride | 4.95 | n.d.—amplification not detected after heating at 55 C. for 24 hrs

Table 2 shows the effect of arginine and its derivatives on Pi DNA polymerase stability and qPCR performance. The formulation was generated by using DNA polymerase stored in CHAPS zwitterionic detergent containing storage buffer supplemented with 0.1 M L-Arginine, 0.1 M L-Arginine Ethyl Ester Dihydrochloride, or 0.1 M Arginiamide Dihydrochloride, respectively. DNA polymerase in storage buffer was pre-incubated at 55 C for 24 hours before it was used for formulation build. Delta Cq (dCq) value was derived by comparing formulation built with preheated polymerase versus control formulation built with polymerase stored at −20 C.

Figure 4:
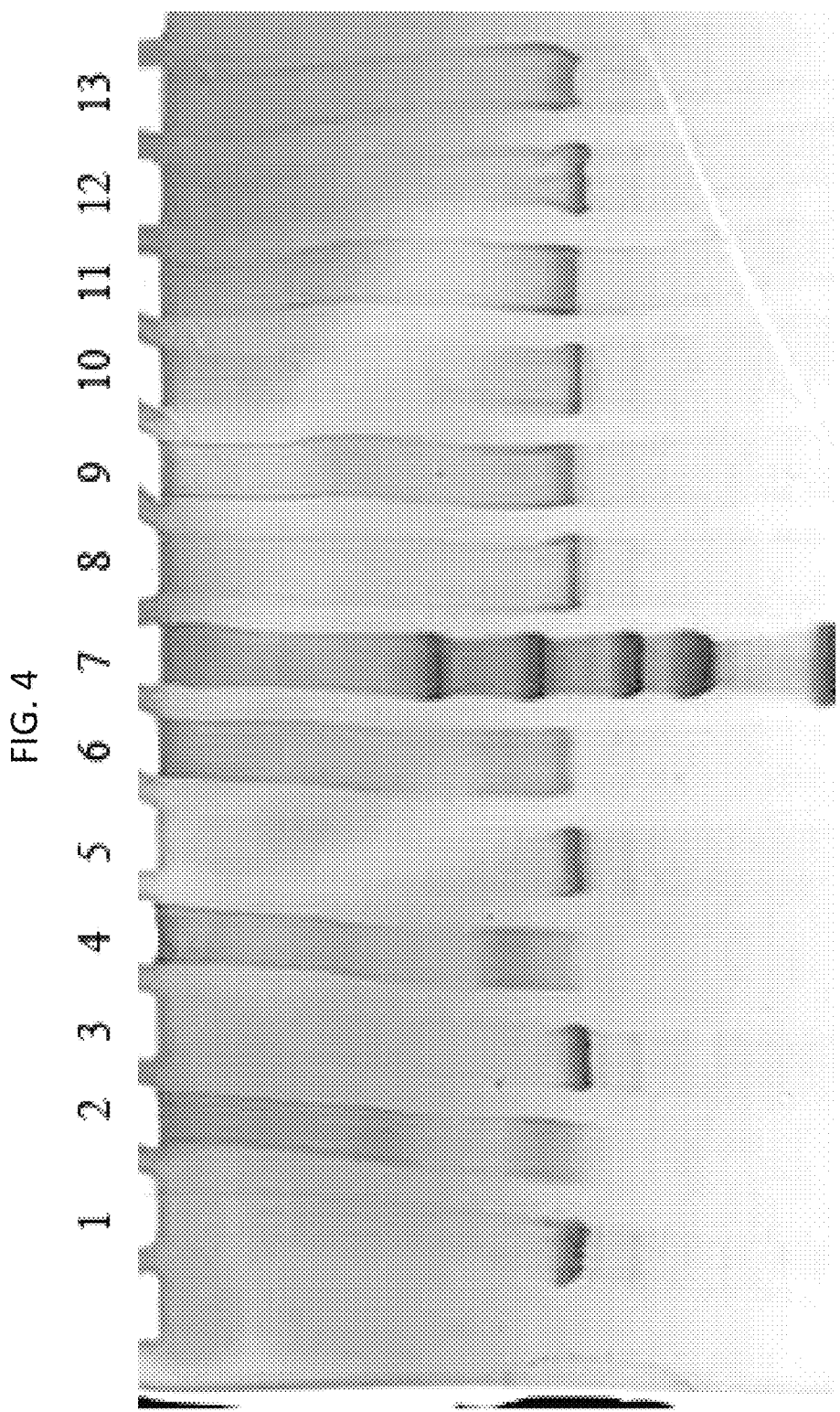
FIG. 4 shows SDS-PAGE analysis of DNA polymerase stability in CHAPS zwitterionic detergent containing storage buffer supplemented with various concentration of L-Arginine. Each lane contains 25 unit of polymerase. Lane 1 and 2 are Pi DNA polymerase in storage buffer stored at −20 C and 55 C for 72 hours, respectively; Lane 3 and 4 are Pi DNA polymerase in storage buffer supplemented with 0.1 M L-Arginine stored at −20 C and 55 C for 72 hours, respectively; Lane 5 and 6 are Pi DNA polymerase in storage buffer supplemented with 0.25 M L-Arginine stored at −20 C and 55 C for 72 hours, respectively; Lane 7 is protein ladder; Lane 8 and 9 are Pi DNA polymerase in storage buffer supplemented with 0.5 M L-Arginine stored at −20 C and 55 C for 72 hours, respectively; Lane 10 and 11 are Pi DNA polymerase in storage buffer supplemented with 0.75 M L-Arginine stored at −20 C and 55 C for 72 hours; Lane 12 and 13 are Pi DNA polymerase in storage buffer supplemented with 1 M L-Arginine stored at −20 C and 55 C for 72 hours.
Figure 5:
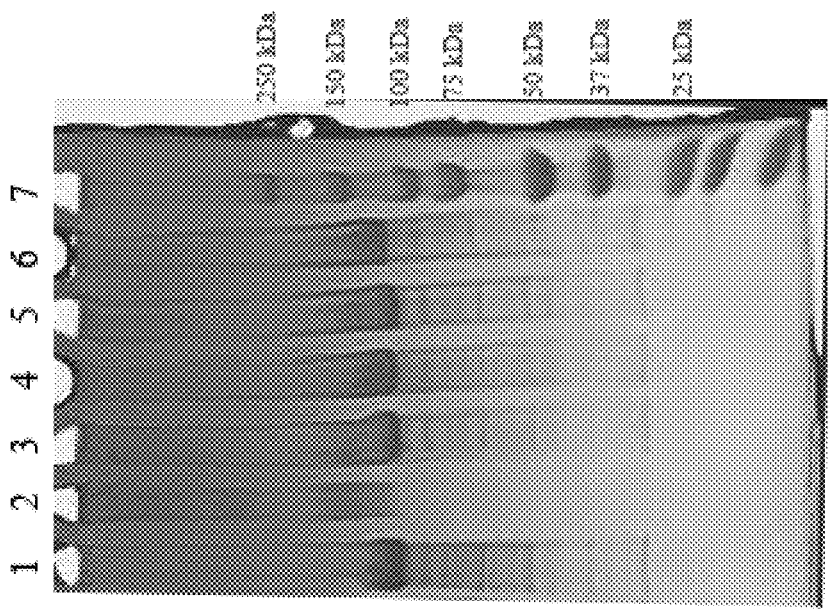
FIG. 5 shows SDS-PAGE analysis of DNA polymerase stability in NP40/Tween20 non-ionic polymeric detergent containing storage buffer supplemented with various concentration of L-Arginine. Each lane contains 100 unit of polymerase. Lane 1 and 2 are Tau DNA polymerase in storage buffer stored at −20 C and 55 C for 24 hours, respectively; Lane 3 and 4 are Tau DNA polymerase in storage buffer supplemented with 0.75 M L-Arginine stored at −20 C and 55 C for 24 hours, respectively; Lane 5 and 6 are Tau DNA polymerase in storage buffer supplemented with 1 M L-Arginine stored at −20 C and 55 C for 24 hours, respectively; Lane 7 is protein ladder.
Figure 6:
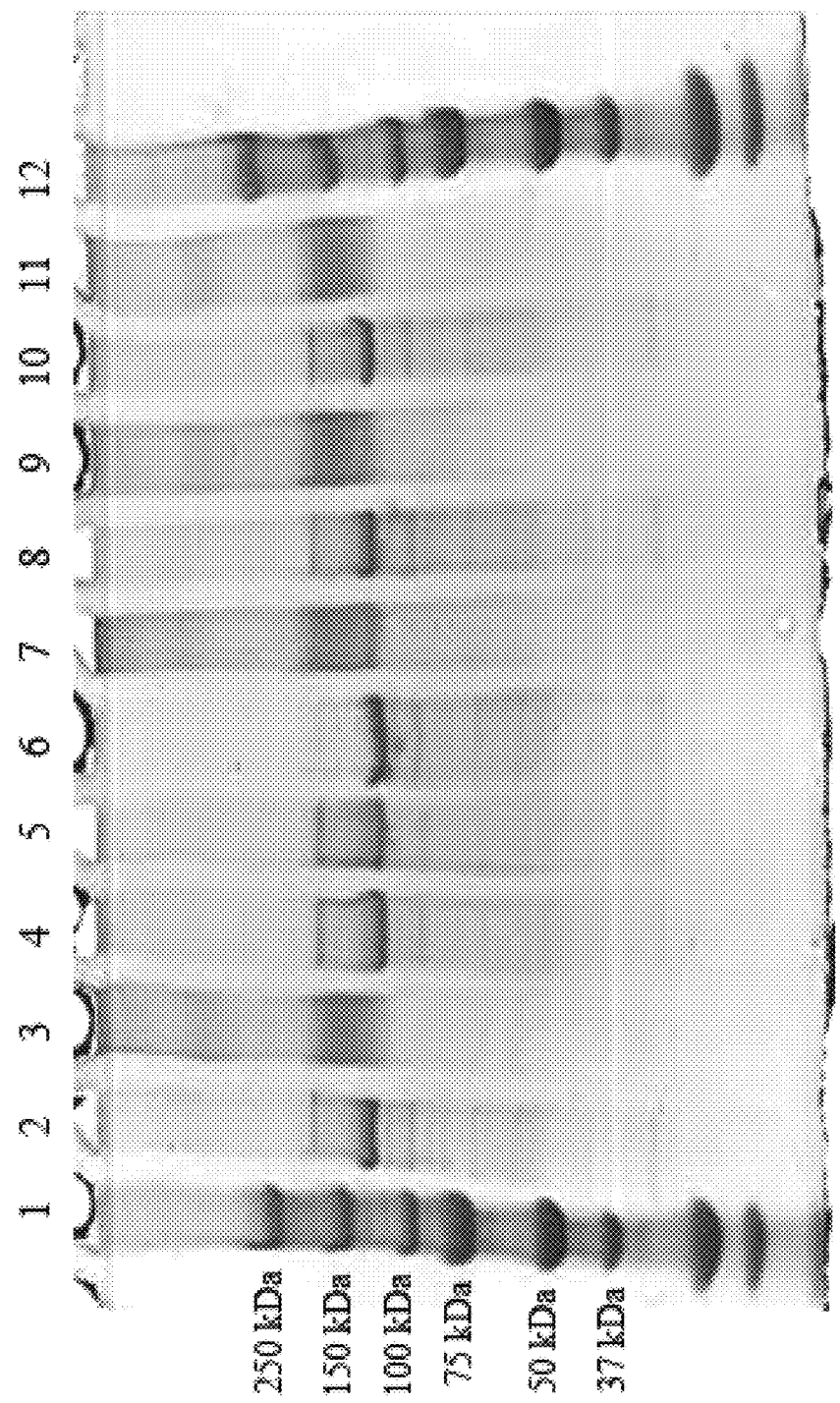
FIG. 6 shows SDS-PAGE analysis of DNA polymerase stability in CHAPS zwitterionic storage buffer supplemented with various additives. Each lane contains 25 unit of polymerase. Lane 1 and 12 are protein ladder; Lane 2 and 3 are Pi DNA polymerase in CHAPS detergent storage buffer stored at −20 C and 55 C for 24 hours, respectively; Lane 4 and 5 are Pi DNA polymerase in CHAPS detergent storage buffer supplemented with 1 M L-Arginine stored at −20 C and 55 C for 24 hours, respectively; Lane 6 and 7 show Pi DNA polymerase in CHAPS detergent storage buffer supplemented with 0.1 M L-Arginine stored at −20 C and 55 C for 24 hours, respectively; Lane 8 and 9 show Pi DNA polymerase in CHAPS detergent storage buffer supplemented with 50 mM Ammonia Chloride stored at −20 C and 55 C for 24 hours, respectively; Lane 10 and 11 show Pi DNA polymerase in CHAPS detergent storage buffer supplemented with 10 mM Magnesium Chloride stored at −20 C and 55 C for 24 hours, respectively.

The polymerase stability enhancement effect of arginine appeared to be universal and independent of detergent. Results of SDS-PAGE analysis of DNA polymerase in either zwitterionic or non-ionic detergent containing storage buffer indicated that arginine protected and stabilized DNA polymerase upon heating at 55° C. for more than 72 hours (FIGS. 4 and 5).

To assess the improvement of long-term storage stability by arginine, accelerated stability test were conducted. Pi DNA polymerase in CHAPS detergent containing storage buffer supplemented with 0.75 M of arginine was incubated at 50° C., 60° C., and 70° C. degree, respectively, for indicated time (Table 3).

TABLE 3

Effect of Arginine supplement on stability and qPCR functional performance of DNA polymerase

| | Pre-incubation temperature | | | | | |
|---|---|---|---|---|---|---|
| | 50° C. | | 60° C. | | 70° C. | |
| Arginine suppl. | --- | + | --- | + | --- | + |
| 2 Days | | | n.d. | −0.40 | | |
| 3 Days | | | n.d. | 0.11 | n.d. | 4.10 |
| 8 Days | n.d. | −0.03 | | | | |
| 11 Days | n.d. | 0.08 | | | | |
| 12 Days | n.d. | 3.79 | | | | | n.d. - amplification not detected after incubation;
positive value - Cq delay as compared to −20 C. control Table 3 shows the effect of arginine in enhancing long-term storage stability of Pi DNA polymerase. Stability improvement is reflected by qPCR performance. The formulation was generated by using DNA polymerase stored in CHAPS zwitterionic detergent containing storage buffer supplemented without (---) or with (+) 0.75 M L-Arginine. DNA polymerase in storage buffer was pre-incubated at corresponding temperature (50 C, 60 C, and 70 C days) and time (2, 3, 8, 11, and 12 days) before it was used for formulation build. Delta Cq value was derived by comparing formulation built with preheated polymerase versus control formulation built with polymerase stored at −20 C. Positive Cq value indicates Cq delay as compared to −20 C control.

These preheated polymerase stocks were used in qPCR reactions to assess their functional activity as compared to a polymerase stock stored at −20° C. As indicated in Table 3, without arginine supplement, preheated Pi thermostable DNA polymerase stocks have no polymerase activity at all temperature tested. In contrast, with Arginine supplement, polymerase activity of preheated polymerase stocks restored. This result suggested that Arginine improves long-term storage stability of thermostable polymerase in stock condition. Although Cq delay was still be observed upon prolonged heating of stock solution at various temperature, the shelf-life of Pi DNA polymerase storage stock supplemented with arginine was found to be significantly improved from 39 days to around 1 year based on the Arrhenius equation predication.

We have also tested a Sso7d-Taq fusion in arginine containing solutions and improved stability has also been observed (data not shown).

Table 4 below shows a thermostability enhancement effect of arginine on various polymerases. (a) Sso-Taq fusion DNA polymerase, (b) MMLV Reverse Transcriptase, and (c) $E.\ coli$ Poly-A polymerase stored in corresponding storage buffer with or without Arginine supplement was heated at corresponding temperature and duration as indicated. Heated polymerase was later used to build reagent formulation, which was subsequently used for qPCR-based performance evaluation following general protocol instructions. Mean Cq-value of replicate is shown.

TABLE 4 a) Sso-Taq DNA polymerase

| | Duration of incubation at 60 C. (Days) | | | |
|---|---|---|---|---|
| Conc. of Arg. (M) | 0 | 3 | 4 | NTC |
| 0 | 20.7 | 27.6 | n.d. | n.d. |
| 0.1 | 20.4 | 20.9 | 20.7 | n.d. |
| 0.5 | 20.3 | 20.7 | 20.5 | n.d. | b) MMLv RTase

| | Duration of incubation at 50 C. (Hours) | | | | |
|---|---|---|---|---|---|
| Conc. of Arg. (M) | 0 | 2 | 4 | 8 | NTC |
| 0 | 28.0 | 36.6 | n.d. | n.d. | n.d. |
| 0.2 | 27.8 | 29.4 | 33.7 | 36.3 | n.d. |
| 0.8 | 27.9 | 28.0 | 28.4 | 29.1 | n.d. | c) $E.\ coli$ Poly-A polymerase

| | Duration of incubation at 55 C. (Minutes) | | | | |
|---|---|---|---|---|---|
| Conc. of Arg. (M) | 0 | 12 | 24 | 48 | NTC |
| 0 | 21.8 | 36.7 | 37.4 | 37.6 | 38.04 |
| 0.4 | 22.7 | 32.7 | 34.4 | 36.0 | 37.06 |
| 0.8 | 24.6 | 29.6 | 31.3 | 33.4 | 39.09 |

Mean Cq value is shown here
n.d. = not detected
NTC = no template control

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A liquid storage solution for a polymerase, the solution comprising,
   the polymerase;
   free arginine, or a salt thereof or arginine derivative or salt thereof; and
   5% or more cryoprotectant,
   wherein the solution is free of detergents.

2. The liquid solution of claim 1, wherein the cryoprotectant is a diol, triol, polyalcohol, monodydric alcohol or a sulfoxide.

3. The liquid solution of claim 1, wherein the free arginine, or a salt thereof or arginine derivative or salt thereof is at a concentration of 0.01-2.5 M.

4. The liquid solution of claim 1, further comprising one or more of a buffer, KCl, ethylenediaminetetraacetic acid (EDTA), or dithiothreitol (DTT).

5. The liquid solution of claim 4, wherein the liquid solution comprises the buffer and the buffer is a Goods buffer.

6. The method of claim 5, wherein the Goods buffer is selected from the group consisting of IViES, BIS-TRIS, ADA, ACES, PIPES, Bis-6Tris Propane, MOPSO, BES, MOPS, TES, HEPES, DIPSO, MPOS, TAPSO, HEPPSO, POPSO, EPPS, Tricine, TRIS, AMP, Bicarbonate, Bicine, Borate, Cacodylate, CAPS, CAPSO, CHES, Citrate, DIPSO, Glycine, Glycylglycine, Phosphate, TAPS, TAPSO, and TEA.

7. The liquid solution of claim 1, wherein the arginine or salt thereof is at a concentration of 0.1-1.0 M.

8. The liquid solution of claim 1, wherein the solution lacks sufficient ingredients to sustain polymerization of a template polynucleotide.

9. The liquid solution of claim 8, wherein the solution lacks at least one of:
   the template polynucleotide; or
   oligonucleotide primers.

10. The liquid solution of claim 1, wherein the solution is at a temperature of −80 to 5° C.

11. The liquid solution of claim 1, wherein the solution is at a temperature of −30 to 5° C.

12. The liquid solution of claim 1, wherein the solution is free of trisaccharides.

13. The liquid solution of claim 1, wherein the polymerase is a thermostable polymerase.

14. The liquid solution of claim 1, wherein the polymerase is a reverse transcriptase.

15. The liquid solution of claim 1, wherein the polymerase is a Family B polymerase.

16. A method of maintaining stability of a polymerase during storage, the method comprising,
   providing the liquid solution of claim 1; and
   storing the solution at between −80 and 5° C. for at least three days.

17. The method of claim 16, wherein the storing is at at between −80 and 5° C.

18. The method of claim 16, wherein the storing is at between −80 and 90° C.

19. The method of claim 16, further comprising following the storing, using the polymerase in an enzymatic reaction.

20. A method of maintaining stability of a polymerase during storage, the method comprising,
   providing a liquid solution comprising the polymerase and 0.01-5.0 M arginine or a salt thereof, wherein the solution is free of detergents; and
   storing the solution for at least three days.

21. The method of claim 20, wherein the storing is at between −80 and 5° C.

22. The method of claim 20, wherein the storing is at between −80 and 90° C.

23. The method of claim 20, further comprising following the storing, using the polymerase in an enzymatic reaction.

* * * * *

UNITED STATES PATENT AND TRADEMARK OFFICE
CERTIFICATE OF CORRECTION

PATENT NO. : 10,053,676 B2
APPLICATION NO. : 14/817064
DATED : August 21, 2018
INVENTOR(S) : Man Cheng Page 1 of 1

It is certified that error appears in the above-identified patent and that said Letters Patent is hereby corrected as shown below:

In the Claims

Column 15
Claim 6, Line 2 reads "selected from the group consisting of IViES, BIS-TRIS," and should be changed to -- selected from the group consisting of MES, BIS-TRIS, --

Signed and Sealed this
Eighteenth Day of August, 2020

Andrei Iancu
*Director of the United States Patent and Trademark Office*